United States Patent [19]
Glover

[11] Patent Number: 6,121,006
[45] Date of Patent: Sep. 19, 2000

[54] IMMUNOASSAY UTILIZING TWO INCUBATIONS WITH LABELED ANTIGEN

[75] Inventor: Justin Mark Glover, Hazlemere, United Kingdom

[73] Assignee: Ortho Clinical Diagnostics, United Kingdom

[21] Appl. No.: 09/141,887

[22] Filed: Aug. 28, 1998

[51] Int. Cl.[7] .............................. G01N 33/53; C12Q 1/70; C12Q 1/28; C07K 16/00
[52] U.S. Cl. ...................... 435/7.2; 530/389.4; 435/7.1; 435/5; 435/28
[58] Field of Search ............................. 530/389.4; 435/5, 435/28, 7.1, 7.2

[56] References Cited

U.S. PATENT DOCUMENTS 4,789,628  12/1988  Nayak ........................................... 435/7
5,683,864  11/1997  Houghton et al. ........................... 435/5

FOREIGN PATENT DOCUMENTS 0 313 986 A2  5/1989  European Pat. Off. .
WO 88/09933  12/1988  WIPO .

Primary Examiner—Hankyel Park
Attorney, Agent, or Firm—Stacey B. Antar

[57] ABSTRACT

The present invention relates to an immunoassay for antibodies against an infectious agent. The present invention also relates to the use of the immunoassay and a kit for performing the immunoassay of the present invention. The immunoassay for antibodies against an infectious agent relates to a method comprising: i. incubating a sample suspected of containing said antibodies with immobilized antigen of the infectious agent and free labeled antigen of the infectious agent; ii. separating immobilized components from non-immobilized components; iii. incubating the immobilized components with further free labeled antigen of the infectious agent and removing non-immobilized components; and iv. determining the amount of labeled antigen immobilized, wherein the amount of label is indicative of the amount of said antibodies present in the sample.

9 Claims, 1 Drawing Sheet

IMMUNOASSAY UTILIZING TWO INCUBATIONS WITH LABELED ANTIGEN

FIELD OF THE INVENTION

The present invention relates to an immunoassay. The present invention also relates to the use of the immunoassay and a kit for performing the immunoassay of the present invention.

BACKGROUND OF THE INVENTION

Immunoassays employ antibodies as analytical reagents for the detection of analytes. Immunoassays are used to detect the presence of an infectious agent by assaying either for the infectious agent or for antibodies raised by the infected host against the infectious agent. The present invention relates to an immunoassay for detecting antibodies against an infectious agent.

Immunoassays for detecting antibodies can involve two incubation steps. In the first incubation, a sample to be tested is incubated with antigens of an infectious agent which have been immobilized on a surface, for instance the surface of a microwell. Any antibodies in the sample against the infectious agent become bound to the antigens on the surface. After a wash step, the second incubation is performed using antigens of the infectious agent labeled with a detectable substance. Labeled antigen will become bound to the antibodies immobilized on the surface. After a further wash step, the amount of label bound to the surface is determined.

A high signal indicates the presence of antibodies against the infectious agent. FIG. 1 gives a schematic representation of such a prior art immunoassay.

A commercially available example of such a prior art immunoassay is the ORTHO™ HIV-1/HIV-2 Ab-capture ELISA test system.

The accurate detection of HIV and other infections is of considerable importance. Early diagnosis of HIV infection enables medical treatment to be started and precautions to be taken in order to limit transmission of the virus. The avoidance of false positives in detecting HIV infection is also of considerable importance.

SUMMARY OF THE INVENTION

The prior art immunoassays have a number of limitations, including limited sensitivity and difficulty in discriminating between weak positive and negative samples. The limitations of the prior art immunoassays are discussed in EP-A-0174652. Accordingly, there is a need for an immunoassay with increased sensitivity and specificity.

The present invention provides an immunoassay for antibodies against an infectious agent comprising:
  i. incubating a sample suspected of containing said antibodies with immobilized antigen of the infectious agent and free labeled antigen of the infectious agent;
  ii. separating immobilized components from non-immobilized components;
  iii. incubating the immobilized components with further free labeled antigen of the infectious agent and then separating immobilized components from nonimmobilized components; and
  iv. determining the amount of labeled antigen immobilized, wherein the amount of label is indicative of the amount of said antibodies present in the sample.

The presence of free labeled antigen in the first incubation of the immunoassay has been found to increase weak positive signals while negative signals remain unchanged.

The presence of free labeled antigen in the second incubation in addition to the first incubation is required, especially if the sample is a strongly positive sample or suspected of being a strongly positive sample. A strongly positive sample is a sample wherein the amount of antibody against the infectious agent is sufficiently high to saturate the immobilized antigen and the free labeled antigen. For example, a strongly positive sample is a sample which is still positive at a dilution of greater than 1/5000.

DETAILED DESCRIPTION OF THE INVENTION

Figure 1:
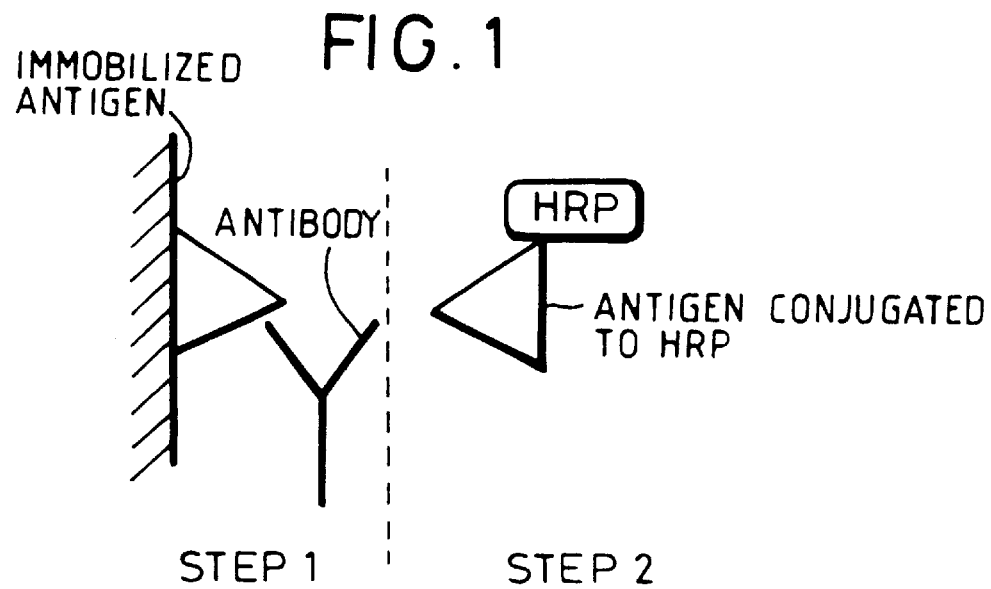
FIG. 1 is a schematic diagram showing a prior art immunoassay.

The term "infectious agent" as used herein means any organism or particle that can infect a patient. Infectious agents include bacteria and viruses. Preferably, the immunoassay of the present invention is for use in detecting antibodies against one or more of HIV-1, HIV-2, hepatitis B virus (HBV) and hepatitis C virus (HCV).

The immunoassay of the present invention can be used to detect the presence of antibodies which are against different infectious agents. Accordingly, the immunoassay of the present invention can be used to detect the presence of more than one infectious agent.

It will be apparent to one skilled in the art that when the immunoassay is used to detect the presence of antibodies against different infectious agents, antigens of each different infectious agent must be used in the immunoassay.

The immunoassay of the present invention must use one and preferably uses two or more antigens for each infectious agent being detected. Preferred antigens are those having an epitope which is easily recognizable and strongly bound by an antibody. It is further preferred that the antigen has an epitope that is stable and not prone to mutation thereby reducing the risk that a mutated form of the infectious agent will not be detected.

Preferably, when the infectious agent is HIV, the antigen is selected from gp120, p24, gp41, qp160, Env10 and Env13 A/L.

Preferably, when the infectious agent is HBV, the antigen is selected from HBs (hepatitis B surface antigen) and HBc (hepatitis B core antigen)

In the immunoassay of the present invention, the antigen is preferably immobilized on a surface. The surface may be a wall of a microtitre well or other receptacle for receiving the sample and/or free labeled antigen, a dipstick or beads. Surfaces suitable for immobilizing an antigen are described in "Immunoassays" (Diamandis, E. P. and Christopoulos T. K. Eds., Academic Press, London (1996)), especially pages 205 to 216.

The antigen may be immobilized via a number of standard techniques known to those skilled in the art. For example, by physical adsorption of the antigen itself or the antigen coupled to a carrier protein or macromolecule (see "Immunoassays", Diamandis, E. P. and Christopoulos T. K. Eds. , Academic Press, London (1996), especially pages 216 to 222 and 229).

The free labeled antigen may be labeled with any type of detectable label provided the label does not interfere substantially with binding of the antigen to the antibody. Suitable labels include: enzymes, such as horseradish peroxidase (HRP) and chloramphenicol acetyl transferase (CAT); digoxygenin (DIG); fluorescein; and radioisotopes such as $^{125}I$, $^{3}H$ and $^{14}C$. Preferably, the antigen is labeled with horseradish peroxidase (HRP).

Depending on the label used, the amount of labeled antigen immobilized is determined using standard methods known to one skilled in the art. For example, if the label is HRP, the degradation of luminol by the enzyme and the associated emission of chemiluminescence can be measured. However, if a radioactive label is used, the presence of the label is measured by detecting the emitted radiation.

If antibodies against different infectious agents are being detected, the free labeled antigens of each different infectious agent may be labeled differently so that it is possible to distinguish between the antibodies against each infectious agent.

The sample can be any fluid or tissue which contains antibodies, such as blood, serum, bone marrow, saliva or urine. However, if the sample is a tissue sample, it may be necessary to break up the tissue in a suitable solution, such as saline, so that the antibodies are present in solution.

Preferably, the sample is blood. In some circumstances, it may be necessary to remove certain components from the blood sample, such as red and white blood cells, before the sample is used. Most preferably, the sample is blood plasma.

Preferably, the immunoassay of the present invention additionally comprises the use of an assay buffer in order to provide a suitable biological environment for performing the immunoassay. Suitable assay buffers are known to those skilled in the art and include phosphate buffers, and may comprise NaCl to increase ionic strength and proteinaceous material to reduce non-specific binding and interferences.

The present invention also provides the use of the immunoassay of the present invention in the diagnosis of the presence of an infectious agent.

Preferably, the infectious agent is HIV-1 or HIV-2.

The present invention further provides a kit adapted for performing the immunoassay of the present invention, comprising:

i) a surface on which an antigen of the infectious has been immobilized or a surface on which an antigen of the infectious agent can be immobilized in combination with means for immobilizing an antigen of the infectious agent;

ii) free labeled antigen;

iii) signal reagent and/or apparatus for detecting the presence of the labeled antigen; and iv) a receptacle for incubating the surface with a sample and/or the free labeled antigen, wherein the receptacle may optionally comprise the surface, wherein the kit is adapted so that free labeled antigen is incubated with the sample and the immobilized antigen.

The surface on which an antigen has been immobilized may be a wall of a microtitre well or other receptacle for receiving the sample and/or free labeled antigen, a dipstick or beads. Surfaces suitable for immobilizing an antigen are described in "Immunoassays" (Diamandis, E. P. and Christopoulos T. K. Eds., Academic Press, London (1996)), especially pages 205 to 216.

The signal reagent and/or apparatus will depend on the label used in the kit. For example, if the label is HRP, the signal reagent may comprise luminol.

Preferably, the kit of the present invention also comprises an assay buffer in order to provide a suitable biological environment for performing the immunoassay.

The present invention is now described further by way of example only with reference to the accompanying figures in which:

In FIG. 1 a patient's sample containing antibody is added to immobilized antigen in the first incubation of the immunoassay. Any unbound antibody is washed off during the wash step. Antigen conjugated to HRP is then added in the second incubation of the immunoassay and binds to any free binding sites of the bound antibody. The amount of bound HRP and consequently bound patient's antibody is measured by the addition of a signal reagent; and In FIG. 2 a patient's sample containing antibody and antigen conjugated to HRP are added to immobilized antigen in the first incubation of the immunoassay. Any unbound components are washed off in the wash step.

Antigen conjugated to HRP is then added in the second incubation of the immunoassay and binds to any free binding sites of the bound antibody. The amount of bound HRP and consequently bound patient's antibody is measured by the addition of a signal reagent.

Comparative Example

Prior art, two step Protocol (see FIG. 1)

Add to an HIV antigen-coated microwell, prepared by passive adsorption of Env10, Env13, Env A/L and p24 (supplied commercially from Chiron) by overnight coating in a borate buffer (pH 9.0, 90mM), 80 µl of sample and 20 µl of assay 30 buffer. Incubate for 25 minutes. Wash with wash buffer. Add 100 µl HRP-labeled antigens (i.e. HRP-labeled Env10, Env13, Env A/L and p24 (supplied commercially from Chiron)) and incubate for 5 minutes. Wash with wash buffer (supplied commercially from Ortho Clinical Diagnostics (O.C.D), Amersham). Add 200 µl signal reagent (supplied commercially from O.C.D, Amersham) and detect the signal using enhanced chemiluminescence.

EXAMPLE 1

Figure 2:
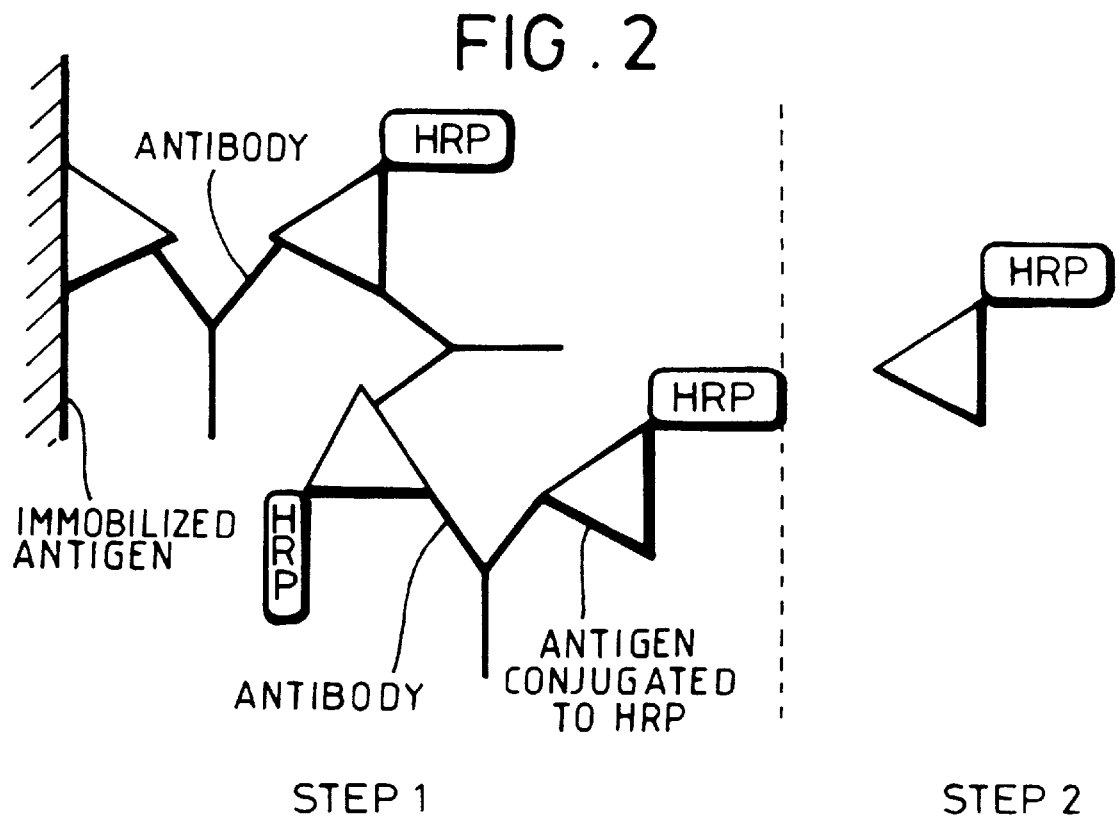
FIG. 2 is a schematic diagram showing the immunoassay of the present invention.

Double HRP labeled antigen Incubation Protocol (see FIG. 2)

Add to an HIV antigen-coated microwell, prepared as above, 80 µl of sample, 20 µl of assay buffer and 20 µl HRP-labeled antigens (as defined above). Incubate for 25 minutes. Wash with wash buffer. Add 100 µl HRP labeled antigen (as defined above) and incubate for 5 minutes. Wash with wash buffer (supplied commercially from O.C.D, Amersham). Add 200 µl signal reagent and detect (supplied commercially from O.C.D, Amersham) the signal using enhanced chemiluminescence.

| Reagent Formulations | | |
|---|---|---|
| Assay Buffer Reagent | | HRP-Labeled Antigen |
| Deionized water | 1000 g | Deionized water |
| Disodium, hydrogen orthophosphate | 0.31 g | Disodium hydrogen orthophosphate |
| Potassium di-hydrogen orthophosphate | 1.09 g | Potassium di-hydrogen orthophosphate |
| Sodium Chloride | 8.2 g | Sodium Chloride |
| KATHON | 5.0 g | KATHON |
| EDTA | 0.35 g | Foetal Calf Serum |
| Antifoam | 0.01 g | Potassium ferricyanide |
| | | TWEEN 20 |
| | | HRP-labeled HIV antigens |

-continued

Reagent Formulations

| Assay Buffer Reagent | HRP-Labeled Antigen |
|---|---|
| | Antifoam |

Results

Using the double HRP-labeled antigen incubation protocol of the present invention, increased differentiation between negative signals and weak positive signals is achieved (see Table 1). This improved differentiation can be used to increase both the sensitivity and the specificity of the immunoassay by positioning the cut-off appropriately.

Seroconversion panel sensitivity is also improved by using the immunoassay of the present invention. From the results shown in Table 2 it can be seen that sample AB2 gives a negative result with the standard assay format but a clear positive result when HRP-labeled antigen is added to the first step of the immunoassay. Sample R1 also gives a stronger positive result with the extra HRP labeled antigen. Both of these samples are key seroconversion samples that are not detected by the majority of commercially available immunoassays.

TABLE 1

Effect on signal by addition of HRP labeled antigen into the first step of a 2 step immunoassay

| | Signal (light units) | |
|---|---|---|
| Sample labeled | Standard Assay | Double HRP Antigen |
| Weak Positives | | |
| Calibrator | 0.68 | 4.08 |
| QCA | 0.12 | 4.74 |
| QCB | 4.54 | 20.56 |
| QCC | 9.80 | 50.36 |
| QCD | 13.27 | 32.13 |
| Negatives | | |
| 1 | 0.07 | 0.10 |
| 2 | 0.02 | 0.02 |
| 3 | 0.02 | 0.03 |
| 4 | 0.02 | 0.02 |
| 5 | 0.03 | 0.03 |
| 6 | 0.02 | 0.03 |
| mean negative result | 0.03 | 0.04 |

Positive signals increased by between 3 and 40 fold. No significant increase in negative results.

TABLE 2

Improved detection of Seroconversion samples by addition of HRP labeled antigen into the first step of the reaction.

| Seroconversion labeled Samples | Normalized Results (>1 = positive) | |
|---|---|---|
| Assay | Standard Assay | Double HRP antigen |
| R1 | 1.70 | 2.32 |
| R2 | 14.81 | 15.41 |

TABLE 2-continued

Improved detection of Seroconversion samples by addition of HRP labeled antigen into the first step of the reaction.

| Seroconversion labeled Samples | Normalized Results (>1 = positive) | |
|---|---|---|
| Assay | Standard Assay | Double HRP antigen |
| E8 | 0.13 | 0.12 |
| E9 | 7.31 | 7.85 |
| E10 | 53.50 | 40.92 |
| AB2 | 0.85 | 1.28 |
| AB3 | 89.06 | 72.25 |
| W8 | 0.11 | 0.09 |
| W9 | 5.86 | 5.83 |
| W10 | 26.13 | 21.17 |

Accordingly, the invention offers the following advantages to the performance of immunoassays:

1. Improved seroconversion sensitivity;
2. Improved dilutional sensitivity (i.e. an increased ability to detect smaller quantities of antibodies); and
3. Improved specificity.

Other embodiments will be evident to those of skill in the art. It should be understood that the example is provided for clarity only and is merely exemplary. The spirit and scope of the present invention are not limited by the above example, but are encompassed by the following claims. All cited materials herein are hereby incorporated by reference.

We claim:

1. An immunoassay for antibodies against an infectious agent comprising:
   i. incubating a sample suspected of containing said antibodies with one or more immobilized antigens of the infectious agent and free labeled antigen of the infectious agent;
   ii. separating immobilized components from non-immobilized components;
   iii. incubating the immobilized components with further free labeled antigen of the infectious agent and removing non-immobilized components; and
   iv. determining the amount of labeled antigen immobilized, wherein the amount of label is indicative of the amount of said antibodies present in the sample.

2. The immunoassay of claim 1 wherein the antibodies are against two or more different infectious agents.

3. The immunoassay of claim 1 wherein two or more antigens of each infectious agent are used.

4. The immunoassay of claim 1 wherein the infectious agent is one or more of HIV-1, HIV-2, HBV and HCV.

5. The immunoassay of claim 2 wherein the infectious agent is HIV-1 and HIV-2.

6. The immunoassay of claim 5 wherein the antigen is one or more of gp120, p24, gp41, gp160, Env10 and Env13 A/L.

7. The immunoassay of claim 1 wherein the infectious agent is HBV.

8. The immunoassay of claim 7 wherein the antigen is one or more of HBs and HBc.

9. The immunoassay of claim 1 wherein the labeled antigen is labeled with horseradish peroxidase.

\* \* \* \* \*